US012637512B2

(12) United States Patent
Su et al.

(10) Patent No.: US 12,637,512 B2
(45) Date of Patent: May 26, 2026

(54) HUMANIZED ANTI-IL-4Rα SINGLE DOMAIN ANTIBODY AND APPLICATION THEREOF

(71) Applicant: REGENECORE BIOTECH CO., LTD, Jiangsu (CN)

(72) Inventors: Zhipeng Su, Jiangsu (CN); Yun Zhang, Jiangsu (CN); Jinguo Meng, Jiangsu (CN); Lefei Wang, Jiangsu (CN); Yao Yao, Jiangsu (CN)

(73) Assignee: REGENECORE BIOTECH CO., LTD, Jiangsu (CN)

( * ) Notice: Subject to any disclaimer, the term of this patent is extended or adjusted under 35 U.S.C. 154(b) by 605 days.

(21) Appl. No.: 18/001,934

(22) PCT Filed: Feb. 24, 2021

(86) PCT No.: PCT/CN2021/077649
§ 371 (c)(1),
(2) Date: Dec. 15, 2022

(87) PCT Pub. No.: WO2022/121118
PCT Pub. Date: Jun. 16, 2022

(65) Prior Publication Data
US 2023/0279123 A1      Sep. 7, 2023

(30) Foreign Application Priority Data

Dec. 9, 2020    (CN) .......................... 202011445635.4

(51) Int. Cl.
| | |
|---|---|
| *C07K 16/28* | (2006.01) |
| *A61K 39/00* | (2006.01) |
| *A61P 11/00* | (2006.01) |
| *A61P 11/06* | (2006.01) |
| *A61P 17/00* | (2006.01) |
| *A61P 31/06* | (2006.01) |
| *A61P 37/02* | (2006.01) |
| *A61P 37/08* | (2006.01) |
| *C07K 16/24* | (2006.01) |

(52) U.S. Cl.
CPC .......... *C07K 16/2866* (2013.01); *A61P 11/00* (2018.01); *A61P 11/06* (2018.01); *A61P 17/00* (2018.01); *A61P 31/06* (2018.01); *A61P 37/02* (2018.01); *A61P 37/08* (2018.01); *C07K 16/244* (2013.01); *A61K 2039/505* (2013.01); *C07K 2317/24* (2013.01); *C07K 2317/31* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *C07K 2319/00* (2013.01)

(58) Field of Classification Search
CPC .............. C07K 16/2866; C07K 16/244; C07K 2317/24; C07K 2317/31; C07K 2317/565; C07K 2317/567; C07K 2317/569; C07K 2317/73; C07K 2317/76; C07K 2317/92; C07K 2319/00; A61P 11/00; A61P 11/06; A61P 17/00; A61P 31/06; A61P 37/02; A61P 37/08; A61K 2039/505; C12N 15/63

See application file for complete search history.

(56) References Cited

U.S. PATENT DOCUMENTS

| | | | |
|---|---|---|---|
| 2018/0371097 A1 | 12/2018 | Morsey et al. | |
| 2022/0411519 A1* | 12/2022 | Wan ...................... | C12N 15/85 |

FOREIGN PATENT DOCUMENTS

| | | |
|---|---|---|
| CN | 104788563 A | 7/2015 |
| CN | 108409860 A | 8/2018 |
| CN | 110105451 A | 8/2019 |
| CN | 110746507 A | 2/2020 |
| CN | 111040035 A | 4/2020 |
| CN | 111518211 A | 8/2020 |
| CN | 111690066 A | 9/2020 |
| IN | 111514292 A | 8/2020 |
| JP | 2016535093 A | 11/2016 |
| JP | 2019525743 A | 9/2019 |
| JP | 2019533719 A | 11/2019 |
| RU | 2016130056 A | 4/2018 |
| WO | 2009081201 A3 | 10/2009 |
| WO | 2017198212 A1 | 11/2017 |
| WO | 2019148405 A1 | 8/2019 |
| WO | 2019157728 A1 | 8/2019 |
| WO | 2019204925 A1 | 10/2019 |
| WO | 2019246003 A1 | 12/2019 |
| WO | 2020147451 A1 | 7/2020 |

OTHER PUBLICATIONS

U.S. Appl. No. 18/714,248. Stable Antibody Preparation. Unpublished. Application Year: 2024. (Year: 2024).*
Extended European Search Report for European Application No. 21901835.5 mailed Jun. 13, 2024.
Vincke , et al., "General Strategy to Humanize a Camelid Single-domain Antibody and Identification of a Universal Humanized Nanobody Scaffold", The Journal of Biological Chemistry; vol. 284, No. 5, Jan. 30, 2009, pp. 3273-3284.

(Continued)

*Primary Examiner* — Brad Duffy
*Assistant Examiner* — Elizabeth A Shupe
(74) *Attorney, Agent, or Firm* — Ballard Spahr LLP

(57) ABSTRACT

Provided is a humanized anti-IL-4Rα single domain antibody. The antibody has complementarity determining regions and humanized and modified framework regions.

9 Claims, 6 Drawing Sheets

Specification includes a Sequence Listing.

(56) References Cited

OTHER PUBLICATIONS

International Search Report and Written Opinion from International Application No. PCT/CN2021/077649 mailed Sep. 13, 2021.
Office Action for Japanese Application No. 2022-580486 mailed Jan. 9, 2024.
Kim , et al., "Engineering of Anti-Human Interleukin-4 Receptor Alpha Antibodies with Potent Antagonistic Activity", Scientific Reports No. 9. https://doi.org/10.1038/s41598-019-44253-9, May 22, 2019, pp. 1-12.
Search Report for European Application No. 21901835.5 mailed Nov. 5, 2025.

* cited by examiner

FIG. 2

HUMANIZED ANTI-IL-4Rα SINGLE DOMAIN ANTIBODY AND APPLICATION THEREOF

INCORPORATION OF THE SEQUENCE LISTING

The present application contains a Sequence Listing submitted herewith containing the file name "38472_0127U1_Sequence_Listing. txt," created on Nov. 4, 2025, and having a size of 28,672 bytes, and is hereby incorporated by reference in its entirety pursuant to 37 C.F.R. § 1.52(e)(5).

SEQUENCE LISTING

A sequence listing submitted in computer readable format is hereby incorporated by reference. The computer readable file, created 14 Dec. 2022 is named NP22727689US_Sequence_Listing_Amended.txt and is 16,287 bytes in size.

TECHNICAL FIELD

The present disclosure relates to the technical field of antibodies, and in particular relates to a humanized anti-IL-4Rα single domain antibody and application thereof.

BACKGROUND

Type 2 inflammatory reactions of a human body is caused by T helper 2 (TH2). These reactions have consistent features and are referred to as allergic diseases, such as asthma and a series of other inflammatory diseases. In conventional anti-inflammatory treatment, generally, broad-spectrum immunosuppressive agents are used to suppress the disease pain, or drugs that specifically target TH2 cell downstream products, e.g., drugs target to IgE, are used to treat the diseases. Compared with the conventional treatment, targeting type 2 cytokines secreted by TH2, i.e., IL-4, IL-5 and IL-13, has shown great potential in the treatment of various immune diseases and achieved better treatment outcomes in patients. Following several disappointing clinical results with therapies targeting IL-4, IL-5 or IL-13 in asthmatics, personalized therapy is employed by investigators for asthma subtypes exhibiting an "allergic" phenotype and results in beneficial therapeutic effects. Recently, the beneficial therapeutic effects have also been achieved in a wider range of asthmatics. This suggests that type 2 inflammation is closely associated with severe asthma if key upstream driving factors in a signaling pathway are appropriately blocked. Furthermore, simultaneous suppression of IL-4 and IL-13 has shown therapeutic effects in diseases often coexisting with asthma, e.g., atopic dermatitis and chronic sinusitis such as nasal polyps, which supports the following hypothesis: targeting key "driving factor pathways" could yield therapeutic effects for many allergic diseases.

Allergic diseases are increasingly becoming a global epidemic. Epidemiological studies have shown an increasing prevalence of food allergies, rhinoconjunctivitis, atopic dermatitis and asthma. Allergy is a systemic type 2 inflammatory reaction to innocuous antigens (allergens) caused by a complex interplay between genetic and environmental factors. This reaction ultimately leads to immunoglobulin E (IgE) production and increased various associated inflammatory immune reactions. From mildness to threat of life, patients may experience a variety of disease severities involving single or multiple organ systems and tissues. Allergic diseases may appear quite different due to their unique organ and tissue manifestations, and are often treated by clinicians with different medical specialties. However, the tendency for multiple allergic diseases to emerge in a concurrent or progressive manner (i.e., "atopic marches") suggests that these diseases may have common underlying driving factors. Along these lines, it has long been recognized that type 2 inflammatory reactions mediated by TH2 are crucial in both asthma and atopic dermatitis (two highly prevalent chronic diseases with distinct tissue-specific manifestations in the lung and skin).

Although initial clinical studies with type 2 pathway regulators are somewhat disappointing, clinical data (identified with biomarkers) from patients with allergic asthma provide support for an important role of three specific type 2 cytokines, i.e., interleukin 5 (IL-5) and sister cytokines IL-4 and IL-13 having a co-receptor (FIG. 1). Mepolizumab (developed by GlaxoSmithKline), a humanized IL-5-specific monoclonal antibody (mAb), shows efficacy in some of patients suffering from asthma and from chronic sinusitis with nasal polyps (CSwNP). In addition, simultaneous blocking of IL-4 and IL-13 signaling using a fully humanized IL-4 receptor subunit α (IL-4Rα) blocking antibody (dupilumab; developed by Regeneron/Sanofi) has been proved to be able to treat three allergic diseases, i.e., atopic dermatitis, CSwNP and asthma. The latest clinical data raises an intriguing possibility that targeting key central "driving factors" may achieve substantial therapeutic effects on allergic diseases characterized by multiple organ-specific clinical manifestations. Now is the time to define and classify allergic diseases, so that treatments can be adjusted according to common immune pathways.

Predominance of type 2 inflammation is a key driving factor for allergic diseases. The type of antigen, in combination with environmental factors and underlying genetic factors, may influence the release of a range of cytokines that cause innate immune cells and lymphoid cells to initiate or propagate a type 2 inflammatory process. At a barrier interface of environmental stimuli, epithelial-derived cytokines such as IL-25, IL-33 and thymic stromal lymphopoietin (TSLP) may initiate type 2 immune reactions or amplify existing type 2 inflammation. These upstream mediators stimulate innate cells to produce type 2 cytokines and also help polarize naive T cells into CD4+TH2 cells. TH lymphocyte subsets are classified according to immune responses associated with specific cytokines and inflammatory mediators specific to each subset. For example, TH1 cells produce interferon-γ (IFNγ); TH2 cells produce IL-4, IL-5 and IL-13; TH9 cells produce IL-9; TH17 cells produce IL-17A, IL-17F, IL-21 and IL22; TH22 cells produce IL-22; and regulatory T cells (TREGs) may produce IL-10. Among other actions, TH2 cells induce B cell proliferation and subsequently experience antibody type switching, resulting in high levels of circulating IgE. Therefore, IgE is a key downstream biomarker of TH2 cell activation. IgE binds to high-affinity IgE receptors (FcεRI) found on basophils and mast cells, and cross-linking of IgE on these cells leads to cell activation and degranulation of various inflammatory mediators. These inflammatory mediators include histamine, prostaglandin, and other proinflammatory cytokines (such as IL-4, IL-5, and IL-13), which amplify the type 2 reactions. In the lower respiratory tract, this type 2 inflammatory environment results in eosinophilia, mucus production, and smooth muscle contraction. These processes, while being important protective immune functions to eliminate parasitic infections, have a pathological effect on innocuous antigens or allergens, leading to allergies.

In addition to the classically defined allergic diseases (including asthma, atopic dermatitis, food allergies, allergic rhinitis, and conjunctivitis), various diseases of unknown etiology also have type 2 clinical features (the most notably features are eosinophilia and/or high serum IgE levels). Such diseases include chronic idiopathic urticaria, CSwNP, and eosinophilic esophagitis.

Although some allergic diseases (such as allergic rhinitis) work well with antihistamines and specific immunotherapy, and nonspecific immunosuppression is the mainstay of treatment for more severe allergic diseases (such as atopic dermatitis and asthma), in both diseases, abnormal inflammatory reactions exacerbate and propagate disease symptoms. Symptoms of severe disease may be effectively relieved by reduction of inflammation by systemic administration of broad-acting immunosuppressive agents (e.g., oral administration of or intravenous injection of corticosteroids, cyclosporine A, methotrexate, azathioprine, or mycophenolate mofetil). The immunosuppressive activity of these agents is achieved by targeting downstream mediators such as transcription factors. For example, corticosteroids bind to a glucocorticoid receptor and inhibit expression of key transcription factors, e.g., nuclear factor-κB (NF-κB), that drive inflammation. Cyclosporin A is a calcineurin inhibitor that may prevent the production of IL-2 (by transcription nuclear factor of activated T cells (NFAT)), which is necessary for T cell activation and proliferation. However, due to the broad action of cyclosporine A and corticosteroids, the systemic immunosuppressive therapy may lead to pleiotropic effects, leading to toxicities such as hydrops retention, glucose intolerance, hypertension, muscle weakness, gastrointestinal intolerance, potential bone loss, suppression of the hypothalamic-pituitary-adrenal axis, and increased susceptibility to infection. Topical administration (i.e., nebulization drugs, topical drops, nasal sprays or creams) may reduce side effects of these immunosuppressive agents. However, topical immunosuppression is insufficient to treat the more severe forms of these diseases. Therefore, more specific therapies are still in great request.

Brutal suppression of inflammation does not provide insight into which immune pathways cause and propagate the disease. For example, the broad-acting drug cyclosporine A is effective in treating psoriasis and atopic dermatitis. In contrast, specific targeting tumor necrosis factor (TNF) in psoriasis and atopic dermatitis result in different clinical efficacy, which suggests that the two skin diseases have different driving pathways. TNF blockers have been approved for the treatment of psoriasis, but have yet to demonstrate sustained efficacy in atopic dermatitis (a type 2 inflammation-driven disease).

Omalizumab (Xolair; Novartis/Genentech), induces more specific immunosuppression in allergic diseases by targeting the ultimate mediator of type 2 inflammation and IgE, the potent trigger for degranulation of mast cell and basophil. This IgE-specific humanized monoclonal antibody is the first monoclonal antibody therapy that is approved for asthma by the regulatory, but is ineffective for atopic dermatitis. Omalizumab reduces the level of free serum IgE, and through this novel anti-inflammatory mechanism, it shows an effect of reducing exacerbations. However, as to the forced expiratory volume in first second (FEV1), namely a measure of lung function, Omalizumab shows little improvement in the forced expiratory volume. Omalizumab also improves the symptoms of co-morbid CSwNP. Omalizumab is also approved for the treatment of chronic idiopathic urticaria refractory to antihistamines. In the pivotal trial, omalizumab shows significant improvement in pruritus and disease activity endpoints. In contrast, in atopic dermatitis, the reduced serum free IgE level is insufficient to achieve a good clinical response. Disease endpoints (eczema area and severity index (EASI), and investigator's global assessment (IGA)) do not improve in patients with moderate atopic dermatitis treated with omalizumab for 16 weeks. In addition, pruritus scores are slightly worsened in the treated patients compared to the placebo group. These results suggest that even in type 2 inflammation-driven diseases, IgE, the final product of the TH2 pathway, is not a consistent regulator of diseases.

Targeting key upstream driving factors rather than downstream mediators of type 2 inflammatory pathways may achieve optimal therapeutic effects in a variety of allergic diseases. To this end, three key type 2 cytokines, IL-4, IL-5 and IL-13, are promising candidates consistently treating allergic inflammatory diseases.

IL-4 is the key differentiation factor driving TH2-type reaction. IL-4 initiates differentiation of T cells to the TH2 subtype and induces production of type 2-related cytokines and chemokines, such as IL-5, IL-9, IL-13, TARC and eotaxin. In B cells, IL-4 induces isotype switching to IgE. IL-4 promotes in vitro differentiation of TH naive T cells into T helper 2. IL-4 deficiency in vivo may result in inhibiting type 2 cytokine production in response to parasitic infection. In turn, IL-4 negatively regulates TH1-type responses associated with IFNγ production and macrophage activation, and thus maintains immune polarization against type 2 responses.

IL-4 and IL-13 are potent mediators of type 2 immunity with overlapping and distinct functions related to their receptor expression patterns. Although IL-4 and IL-13 share only 25% amino acid homology, the cytokines share a common moiety of receptor, IL-4Rα. This receptor binds to a unique accessory chain to induce signaling. IL-4Rα is expressed on both hematopoietic and non-hematopoietic cells. However, differential expression of the accessory chains in different cells has revealed the functional differences of IL-4Rα (FIG. 1). A type 1 receptor consists of IL-4Rα and a common γ chain, and the latter is found only in hematopoietic cells. A type 2 receptor complex consists of IL-4Rα and IL-13Rα1, and the latter is found in many non-hematopoietic cells such as keratinocytes, hair follicles, epidermal sebaceous and sweat glands, nasal and bronchial epithelial cells, smooth muscle cells and fibroblasts. IL-4 signals through both the type 1 and type 2 receptor complexes, whereas IL-13 signals only through the type 2 receptor complex. This is because IL-13 binds to its own primary binding chain (IL-13Rα1), while IL-4 mainly binds to IL-4Rα.

Additionally, the two cytokines have different potencies and signaling kinetics. The strong binding of IL-4 to IL-4Rα is independent of γ chain or the IL-13Rα1 binding affinity (KD), whereas the presence of IL-4Rα increases the binding affinity of IL-13 to IL-13Rα1 (KD changes from 10 mM to 30 pM). Furthermore, the type 2 receptor of IL-4 is involved in a faster time course of activated intracellular signaling than IL-13. In mouse models of parasitic infection and allergy, the physiological differences between IL-4 and IL-13 are analyzed by knocking out cytokines and overexpressing phenotypes. Careful examination of these phenotypes as follows may support the following hypothesis: IL-4 is the central medium for TH2 cell differentiation, B cell growth, initiation of isotype class switching (especially IgE) and eosinophil recruitment. IL-13, although has certain redundancy in these proinflammatory processes, plays other roles in mediating goblet cell proliferation and smooth muscle contraction, which may be related to the unique expression pattern of the type 2 receptor complex and local production of cytokines.

Both IL-4 and IL-13 mediate IgE production through activity on B cells. Knockout of IL-4 or IL-13 in mice results in severe defects in allergen-challenged IgE. Although IL-4 may initiate and promote isotype switching and B cell growth, there is evidence that IL-13 may also bind to activated human B cells. This suggests that IL-13 contributes to continuous IgE production and explains the phenotype observed in knockout mice.

IL-4, IL-5 and IL-13 may promote eosinophilia in tissue and blood with type 2 inflammation. IL-5 is a potent eosinophil factor, and is responsible for growth, differentiation, survival and mobilization of bone marrow, and migration from bone marrow to blood. IL-5 binds to a cytokine-specific subunit receptor IL-5Rα that forms a complex with a shared signaling subunit β chain. Granulocyte-macrophage colony stimulating factor (GM-SCF) and IL-3 also require β chain for signaling. IL-5Rα is highly expressed in eosinophils and eosinophil progenitor cells, and is also present in basophils. In the absence of IL-5 (either by gene knockout or after treatment with IL-5-specific antibodies), allergen-challenged eosinophilic responses in blood and tissue are abolished.

The production of type 2 upstream cytokines may promote expression through epithelial derived cytokines IL-25, IL-33 and TSLP, and may be released at the barrier interface after tissue damage or allergen exposure. The activity of these epithelial-derived cytokines to a variety of congenital cell types (e.g., type 2 innate lymphoid cells and mast cells) may induce the production of IL-4, IL-5 and IL-13, and may also promote TH2 response. In particular, IL-33 acts as "alarmin" (a signal of cell or tissue damage), and may polarize naive T cells into TH2 cells and amplify the existing type 2 response. Together with IL-25, IL-33 also induces innate lymphoid cells to produce high levels of type 2 cytokines, especially IL-5 and IL-13. TSLP promotes the production of cytokines in basophils, monocytes and natural killer T cells, and also activates dendritic cells to initiate and activate TH2 cells.

In conclusion, IL-4, IL-5 and IL-13 are pleiotropic, coordinate type 2 immune response, and play different roles, i.e., IgE production and eosinophilia, in driving the expression of activation markers in type 2 and TH2 pathways. Preclinical data provides conclusive evidence that asthma and atopic dermatitis are both driven by these mediators of type 2 inflammation. Transgenic mice overexpressing all three type 2 cytokines IL-4, IL-5, and IL-13 spontaneously develop asthma like lung disease and atopic dermatitis-like skin disease, characterized by exaggerated type 2 reactions, i.e., high serum IgE levels, extensive cellular infiltration (including eosinophils and lymphocytes) in the skin and lungs, skin thickening, and airway epithelial hypertrophy. Further studies have shown that IL-4 and IL-13 are independently sufficient to cause similar pathology. These preclinical data suggest that IL-4 and IL-13 are key proximal disease-driving factors.

In addition, humanized antibodies mainly refer to antibodies obtained by engineering and re-expressing non-human monoclonal antibodies by gene cloning and DNA recombination technology. Most of the amino acid sequences of the humanized antibodies are replaced by human sequences, which basically retains the affinity and specificity of the parent monoclonal antibodies, reduces the heterogeneity, and is beneficial to application in humans. At present, there is a lack of humanized antibody of a camel-derived single domain antibody targeting IL-4Rα.

SUMMARY

An objective of the present disclosure is to provide a humanized anti-IL-4Rα single domain antibody and application thereof. The anti-IL-4Rα single domain antibody according to the present disclosure, which has been humanizedly modified, retains the affinity and inhibition of a tumor cell proliferation, and effectively reduces the immune side reaction.

The present disclosure is implemented as follows:

In one aspect, the present disclosure provides a humanized anti-IL-4Rα single domain antibody having complementarity determining regions comprising CDR1, CDR2 and CDR3 and framework regions comprising FR1, FR2, FR3 and FR4.

An amino acid sequence of CDR1 is as shown in SEQ ID NO. 3, an amino acid sequence of CDR2 is as shown in SEQ ID NO. 12, and an amino acid sequence of CDR3 is as shown in SEQ ID NO. 18.

An amino acid sequence of FR1 is as shown in SEQ ID NO. 2, an amino acid sequence of FR2 is selected from any one of SEQ ID NO. 4-11, an amino acid sequence of FR3 is selected from any one of SEQ ID NO. 13-17, and an amino acid sequence of FR4 is as shown in SEQ ID NO. 20 or 21.

On the basis of a camel-derived anti-IL-4Rα single domain antibody having a sequence of SEQ ID NO. 22, the inventors of the present disclosure obtain the humanized anti-IL-4Rα single domain antibody that retains the affinity and inhibition of a tumor cell proliferation, and effectively reduces the immune side reaction by means of scientific and reasonable humanized modification at a suitable location.

The complementarity determining regions and frameworks are connected in the following order to form a primary sequence structure of the single domain antibody of the present disclosure: FR1-CDR1-FR2-CDR2-FR3-CDR3-FR4.

In an optional embodiment, the amino acid sequence of FR2 is as shown in SEQ ID NO. 11, the amino acid sequence of FR3 is as shown in SEQ ID NO. 15, and the amino acid sequence of FR4 is as shown in SEQ ID NO. 21.

Compared with other humanized single domain antibodies, the single domain antibody of this embodiment exhibits more excellent technical effects, and has higher affinity and less immune side reaction.

In another aspect, the present disclosure provides a fusion protein, which comprises the anti-IL-4Rα single domain antibody as described above.

The single domain antibody according to the present disclosure may be fused with any other proteins or substances to achieve different purposes. For example, the single domain antibody is combined with fluorescent proteins, enzymes or radioactive elements to enable easy assay, or fused with drug molecules for treating IL-4Rα-mediated related diseases to achieve a better therapeutic effect. The type of protein fused with the single domain antibody may be reasonably selected by those skilled in the art according to actual needs or purposes, and the resulted fusion protein all falls within the protection scope of the present disclosure, regardless of type of fused substance with the single domain antibody.

In another aspect, the present disclosure provides a bispecific antibody, which comprises the anti-IL-4Rα single domain antibody as described above.

Based on the sequence or structure of the single domain antibody provided in the present disclosure, those skilled in the art may easily think of fusing the single domain antibody with other specific antibodies to obtain bispecific or multi-specific antibodies that can specifically bind to two or more antigens. This is easily accomplished by those skilled in the art. Therefore, the bispecific antibodies, regardless of the kind of fused antibody with the single domain antibody, all falls within the protection scope of the present disclosure.

In another aspect, the present disclosure provides application of the anti-IL-4Rα single domain antibody as described above, the fusion protein as described above, or the bispecific antibody as described above in preparation of an IL-4Rα-targeted drug for treating a disease.

The single domain antibody, the fusion protein and the bispecific antibody according to the present disclosure may be used for any diseases with IL-4Rα as the therapeutic target, comprising but not limited to asthma, allergic dermatitis, eczema, arthritis, herpes, chronic primary urticaria, scleroderma, hypertrophic cicatrix, chronic obstructive pulmonary disease, atopic dermatitis, idiopathic pulmonary fibrosis, Kawasaki disease, sickle cell disease, Graves' disease, Sjogren's syndrome, autoimmune lymphoproliferative syndrome, autoimmune hemolytic anemia, Barrett's esophagus, autoimmune uveitis, tuberculosis, and nephropathy.

In another aspect, the present disclosure provides a drug for treating a disease, comprising the anti-IL-4Rα single domain antibody as described above, the fusion protein as described above, or the bispecific antibody as described above, and a pharmaceutically acceptable excipient.

The pharmaceutically acceptable excipient refers to pharmaceutical excipients in the field of pharmacy, such as diluents, fillers, binders, wetting agents, absorption enhancers, surfactants, disintegrants, adsorption carriers, lubricants, etc. In addition, other excipients, such as flavoring agents, sweeteners, and the like, may also be added. That is, the excipients are one or two or more of diluents, fillers, binders, wetting agents, absorption enhancers, surfactants, disintegrants, adsorption carriers, lubricants, flavoring agents, and sweeteners. Those skilled in the art may make reasonable choices as needed.

In another aspect, the present disclosure provides an isolated nucleic acid molecule encoding the anti-IL-4Rα single domain antibody as described above.

It should be noted that, based on the present disclosure, those skilled in the art may easily obtain a polynucleotide molecule encoding the above-mentioned single domain antibody and fusion proteins by means of conventional techniques in the art, and based on the degeneracy of codons, the polynucleotide molecule is variable with a variety of specific base sequence. Based on this, regardless of the variation, the polynucleotide molecule falls within the protection scope of the present disclosure as long as it can encode the single domain antibody or fusion protein of the present disclosure.

In another aspect, the present disclosure provides a vector or recombinant cell containing the nucleic acid molecule as described above.

In another aspect, the present disclosure provides a method for preparing the anti-IL-4Rα single domain antibody as described above comprising: culturing a recombinant cell, and isolating and purifying the single domain antibody from the culture product, the recombinant cell comprising a recombinant expression vector comprising the aforementioned nucleic acid molecule.

It should be noted that the single domain antibody, the fusion protein and the antibody of the present disclosure may be prepared by chemical synthesis or genetic engineering techniques, or other methods. No matter what method is used for preparing the single domain antibody, the fusion protein or the antibody of the present disclosure, it all falls within the protection scope of the present disclosure.

BRIEF DESCRIPTION OF THE DRAWINGS

To describe the technical solutions of the embodiments of the present disclosure more clearly, the following briefly describes the accompanying drawings for describing the embodiments. It should be understood that, the following accompanying drawings show only some embodiments of the present disclosure, which cannot be considered as limitation on the scope. A person of ordinary skill in the art may still derive other accompanying drawings from such accompanying drawings without creative efforts.

FIG. 2 shows a sequence alignment result of some clones after humanization of an anti-IL-4Rα monoclonal antibody 4E9;

DETAILED DESCRIPTION OF THE EMBODIMENTS

Figure 1:
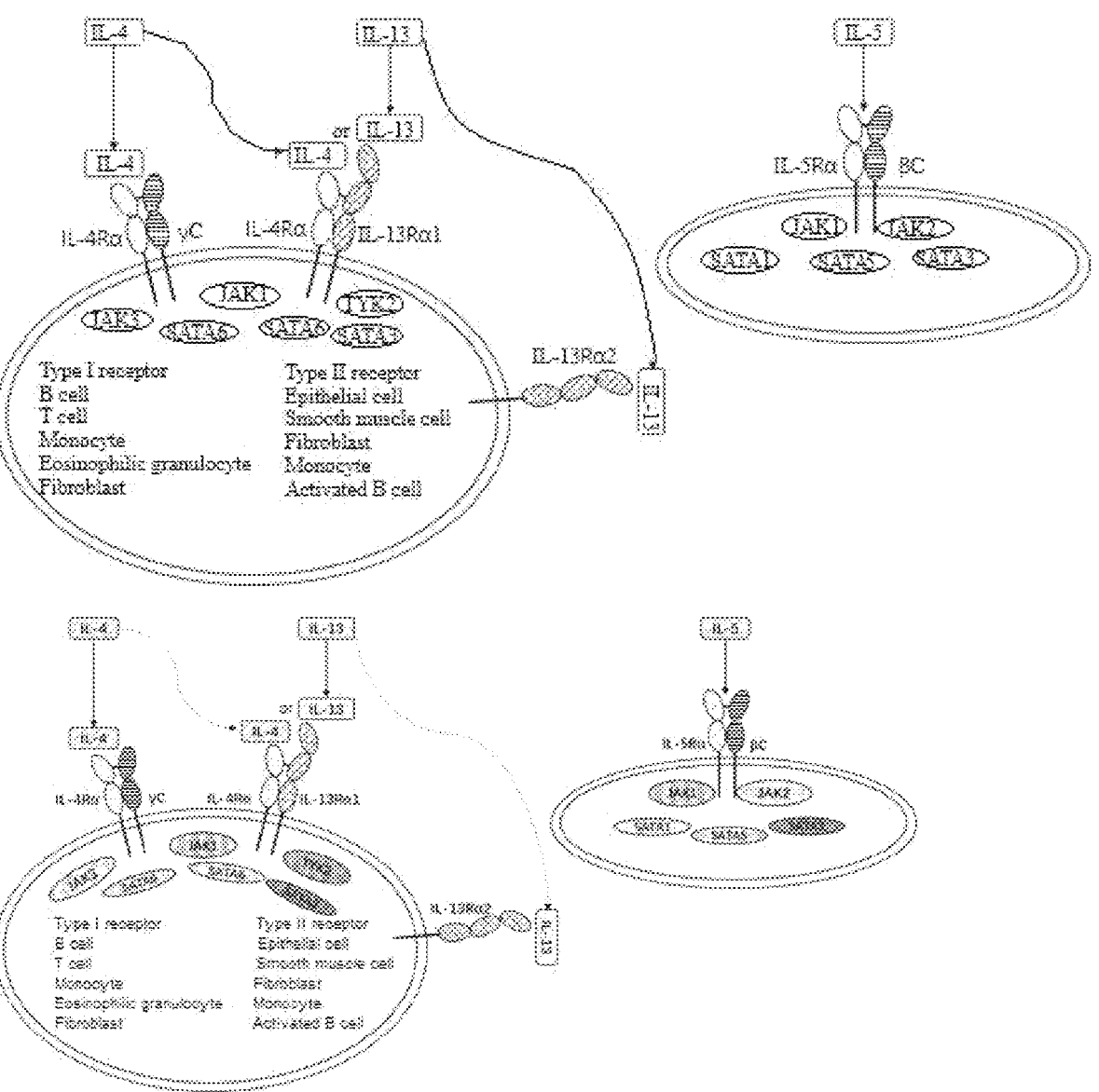
FIG. 1 is a schematic diagram of IL4/IL-13 and IL-5 signaling pathways.

To make the objective, technical solutions and advantages of the embodiments of the present disclosure clearer, the technical solutions in the embodiments of the present disclosure will be described clearly and completely below. If specific conditions are not indicated in the embodiments, it is carried out in accordance with the conventional conditions or conditions suggested by manufacturers. The reagents or instruments used without the manufacturer's indication are conventional products that can be purchased from the market.

The features and performance of the present disclosure will be further described in detail below in conjunction with the examples.

Example 1

Humanized Modification

Humanized modification was carried out on the basis of an anti-IL-4Rα single domain antibody 4E9 (named 4E9-V0) of SEQ ID NO. 22.

Figure 2:
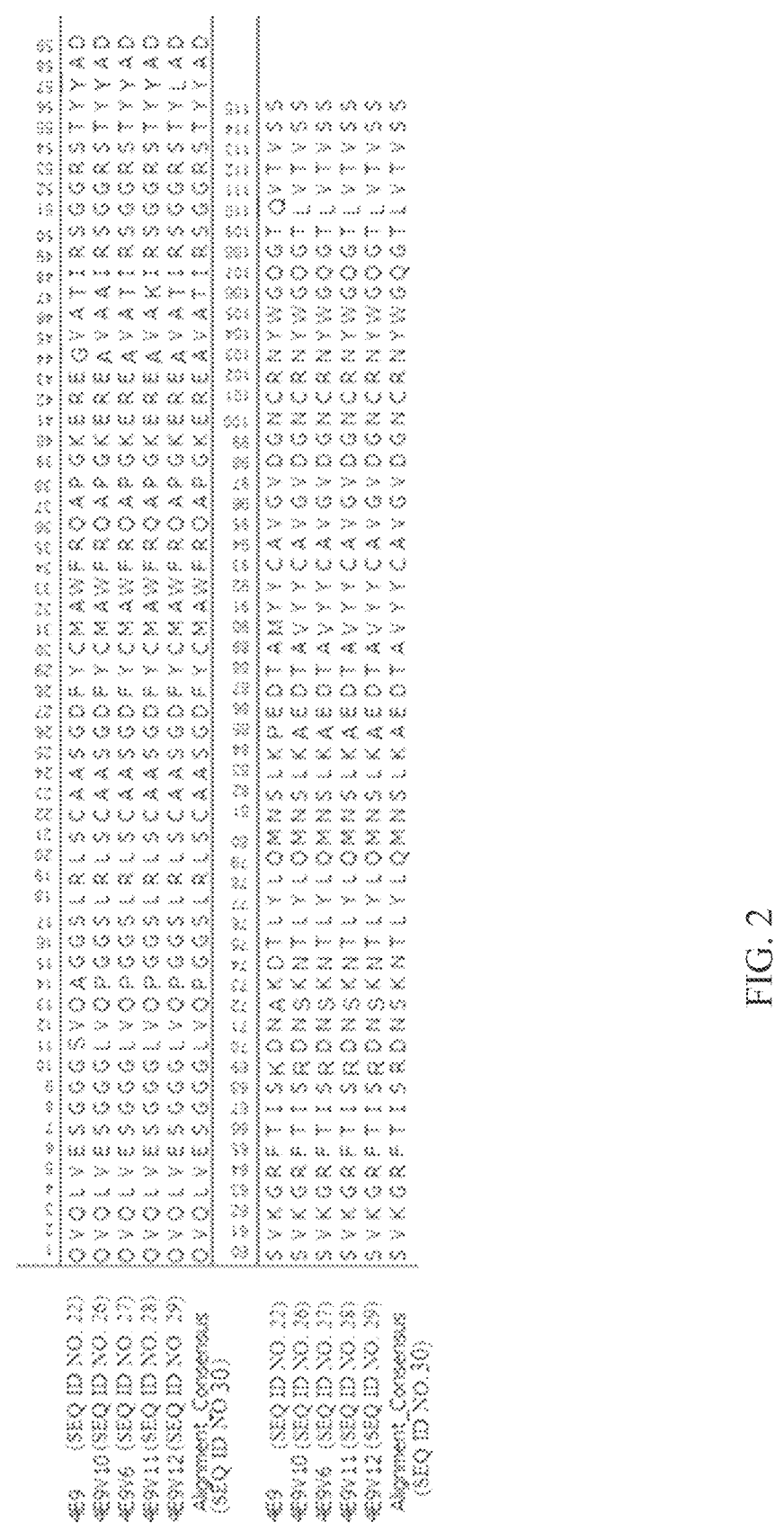

The sequences of the modified humanized single domain antibodies (named 4E9 V1-V14, respectively) are shown in Table 1, and alignment results of partial humanized antibody sequences are shown in FIG. 2.

TABLE 1

| | \multicolumn{7}{c}{Sequence identifier (SEQ ID NO.) corresponding to each region of each humanized single domain antibody} | | | | | | |
| --- | --- | --- | --- | --- | --- | --- | --- |
| | FR1 | CDR1 | FR2 | CDR2 | FR3 | CDR3 | FR4 |
| 4E9-V0 | 1 | 3 | 4 | 12 | 13 | 18 | 20 |
| 4E9-V1 | 2 | 3 | 5 | 12 | 14 | 18 | 21 |
| 4E9-V2 | 2 | 3 | 6 | 12 | 14 | 18 | 21 |
| 4E9-V3 | 2 | 3 | 6 | 12 | 15 | 18 | 21 |
| 4E9-V4 | 1 | 3 | 4 | 12 | 13 | 19 | 20 |
| 4E9-V5 | 2 | 3 | 5 | 12 | 14 | 19 | 21 |
| 4E9-V6 | 2 | 3 | 7 | 12 | 15 | 18 | 21 |
| 4E9-V7 | 2 | 3 | 8 | 12 | 16 | 18 | 21 |

TABLE 1-continued

| | \multicolumn{7}{c}{Sequence identifier (SEQ ID NO.) corresponding to each region of each humanized single domain antibody} | | | | | | |
| --- | --- | --- | --- | --- | --- | --- | --- |
| | FR1 | CDR1 | FR2 | CDR2 | FR3 | CDR3 | FR4 |
| 4E9-V8 | 2 | 3 | 9 | 12 | 16 | 18 | 21 |
| 4E9-V9 | 2 | 3 | 10 | 12 | 15 | 18 | 21 |
| 4E9-V10 | 2 | 3 | 11 | 12 | 15 | 18 | 21 |
| 4E9-V11 | 2 | 3 | 8 | 12 | 15 | 18 | 21 |
| 4E9-V12 | 2 | 3 | 7 | 12 | 16 | 18 | 21 |
| 4E9-V13 | 2 | 3 | 7 | 12 | 17 | 18 | 21 |
| 4E9-V14 | 2 | 3 | 7 | 12 | 14 | 18 | 21 |

Example 2

Assay for Humanized Single Domain Antibodies Neutralizing IL-4-Induced or IL-13-Induced TF1 Cell Proliferation (1) TF-1 cells passaged 3-4 times after recovery were plated in a 96-well plate at 10000 cells/well.

(2) Different Tabs and the humanized single domain antibodies in Table 1 were formulated into 10 μg/mL solutions, and subjected to 5-fold gradient dilution.

(3) The Tab antibodies (obtained referring to a method disclosed in the Chinese invention patent application no. CN202010576200.7 titled with "Anti-IL-4Rα single domain antibody as well as application and drug") and the humanized single domain antibodies both subjected to gradient dilution were mixed with IL-4 or IL13 of EC80 concentration (obtained referring to the method disclosed in the Chinese invention patent application no. CN202010576200.7 titled with "Anti-IL-4Rα single domain antibody as well as application and drug") at 1:1 to prepare a mixed solution. EC80 is defined as follows: EC80, namely the concentration for 80% of maximal effect (EC80), refers to a concentration that can cause 80% of the maximal effect.

(4) The mixed solution in the previous step was added into cell culture wells in an equal volume to the cell culture solution.

(5) After incubation for 72 h, the cell viability was detected with a luminescence cell viability assay kit.

Figure 3:
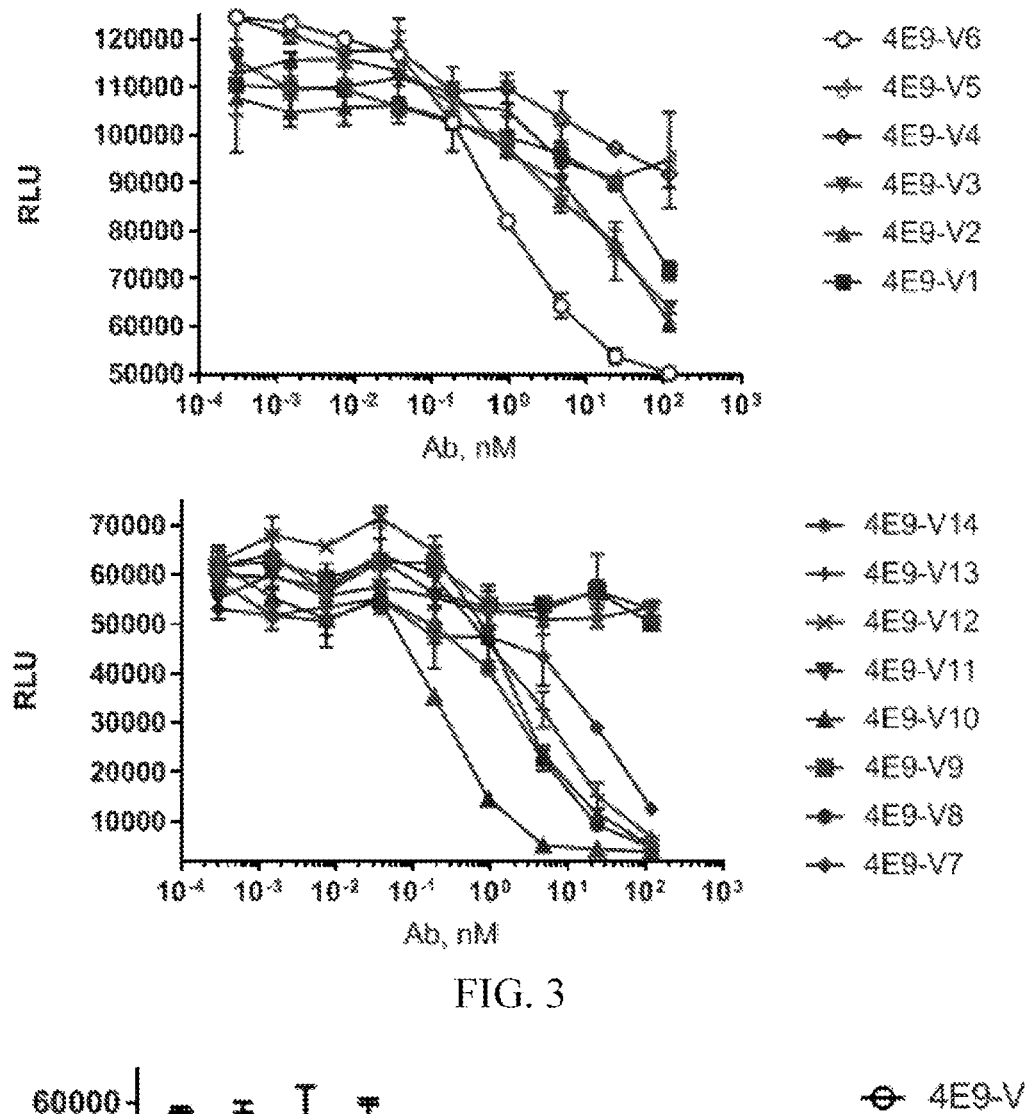
FIG. 3 shows assay results of different humanized 4E9 antibody clones neutralizing IL-4-induced TF-1 proliferation.
Figure 4:
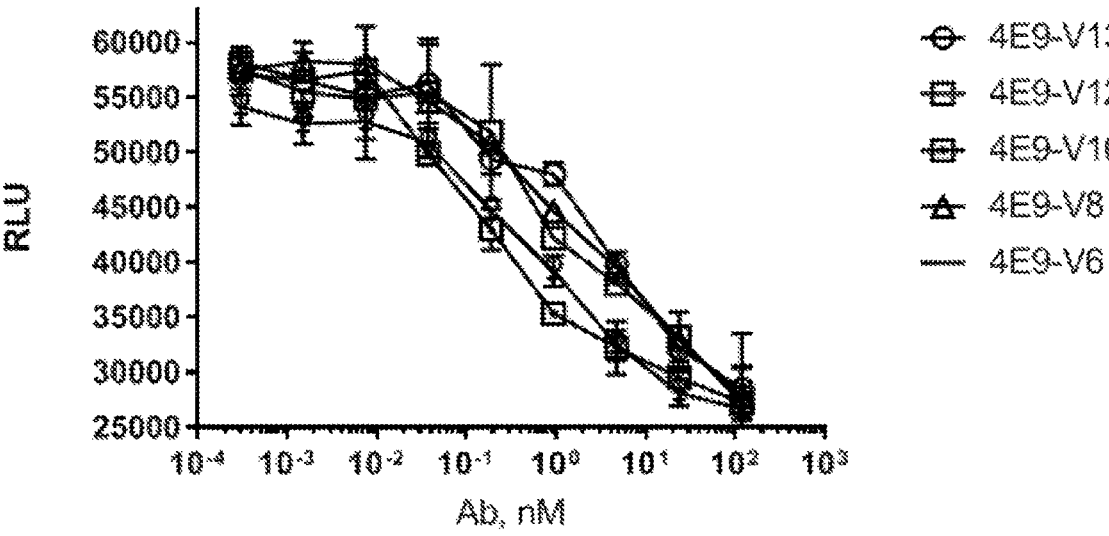
FIG. 4 shows assay results of humanized 4E9 antibody clones neutralizing IL-13-induced TF-1 proliferation.

(6) The EC50 concentrations of different humanized single domain antibodies for neutralizing IL-4-induced or IL13-induced TF-1 cell proliferation was calculated according to the assay results. EC50, namely the concentration for 50% of maximal effect (EC50), refers to the concentration that can cause 50% of the maximal effect. The results are shown in Table 2, Table 3, FIG. 3 and FIG. 4.

TABLE 2

| \multicolumn{8}{c}{Assay results of humanized anti-IL-4Rα single domain antibodies neutralizing IL-4-induced TF-1 proliferation} | | | | | | | |
| --- | --- | --- | --- | --- | --- | --- | --- |
| Antibody name | 4E9-V1 | 4E9-V2 | 4E9-V3 | 4E9-V4 | 4E9-V5 | 4E9-V6 | 4E9-V7 |
| EC50 (nM) | 56898284406318 | 52.08 | 13.84 | 2.917e+20 | 0.7460 | 0.7070 | 185.0 |
| Antibody name | 4E9-V8 | 4E9-V9 | 4E9-V10 | 4E9-V11 | 4E9-V12 | 4E9-V13 | 4E9-V14 |
| EC50 (nM) | 2.768 | 0.7519 | 0.2708 | 1880000 | 2.031 | 4.521 | 18630000 |

TABLE 3

| \multicolumn{6}{c}{Assay results of humanized anti-IL-4Rα single domain antibodies neutralizing IL-13-induced TF-1 proliferation} | | | | | |
| --- | --- | --- | --- | --- | --- |
| | 4E9-V6 | 4E9-V8 | 4E9-V10 | 4E9-V12 | 4E9-V13 |
| EC50 (nM) | 0.7595 | 3.107 | 0.1798 | 2.111 | 4.204 |

The results show that among all humanized antibodies, the 4E9-V10 antibody has the strongest cell proliferation neutralizing ability and has an EC50 of 0.27 nM, 4E9-V1 has the worst effect, and 4E9-V6, 4E9-V8, 4E9-V12 and 4E9-V13 have certain neutralizing effects.

Example 3

Assay for Thermal Stability of Humanized Single Domain Antibodies by Differential Scanning Assay Method:

(1) To an 8-tube strip or a 96-well PCR plate, 45 μL of a solution of 0.1 mg/mL aforementioned humanized single domain antibodies was added, followed by 5 μL of a 100×Sypro orange dye. The dye was at a final concentration of 5×. 3 replicates were made for each sample, with 1×PBS as a blank.

(2) A Melt curve assay was carried out, with a reporter group of ROX and a quencher of None, according to a heating program of 25° C. for 5 min and a scanning range of 25° C.-95° C., at a heating rate of 1% (about 1° C./min).

(3) The temperature corresponding to the maximum value of the first derivative of the melting curve was taken as the denaturation temperature (Tm value) of the protein.

The assay results are as shown in Table 4.

TABLE 4

| Sample name | Tm value (° C.) |
| --- | --- |
| 4E9-V13 | 65.1 |
| 4E9-V12 | 65 |
| 4E9-V10 | 64.6 |
| 4E9-V6 | 64.5 |

TABLE 4-continued

| Sample name | Tm value (° C.) |
| --- | --- |
| 4E9-V7 | 64.3 |
| 4E9-V14 | 64.2 |
| 4E9-V11 | 64.1 |
| 4E9-V4 | 64.1 |
| 4E9-V9 | 64 |
| 4E9-V5 | 63.8 |
| 4E9-V8 | 63.5 |
| 4E9-V1 | 63.3 |
| 4E9-V2 | 63.2 |
| 4E9-V3 | N/A |

The results show that among all the humanized single domain antibodies, 4E9-V13 has the highest thermal stability, 4E9-V3 has the lowest undetectable thermal stability, and 4E9-V10 has the third highest thermal stability among all the antibodies.

Example 4

Determination of Affinity of Humanized Single Domain Antibodies

Preparation of an SD buffer: an appropriate amount of bovine serum albumin and Tween 20 were dissolved in 1×PBS (pH 7.4), so that the mass (or volume) fractions of the bovine serum albumin and the Tween 20 were 0.1% and 0.02% respectively. The IL-4Rα binding molecules (the aforementioned partially humanized single domain antibodies) were formulated with the SD buffer to a concentration of 10 μg/mL.

Preparation of an antigen working solution: an antigen was firstly formulated to 200 nM with the SD buffer, and then subjected to 2-fold gradient dilution. A total of 5 concentration gradients were set, in addition to the SD buffer as a blank control.

Preparation of a regenerating solution: an appropriate amount of a 0.1 M glycine stock solution was diluted 10 times in deionized water and mixed well to obtain the regenerating solution.

Assay steps: Octet 96 and Data Acquisition software in the supporting computer were run. The bottom and sides of an acquisition probe were cleaned using a lens tissue with an appropriate amount of 75% ethanol, and the instrument was preheated for 15 min or more. Sensor pre-wetting: before the assay, the Sensor was soaked in the SD buffer for 10 min or more for later use. Then, the machine procedure was set according to: baseline→antibody→baseline→antigen binding→antigen dissociation→sensor regeneration for assay operation. The assay results are shown in Table 5.

TABLE 5

| Antibody name | KD(M) | KD Error | Ka(1/Ms) | Ka Error | Kd(1/s) | Kd Error | $X^2$ | $R^2$ |
| --- | --- | --- | --- | --- | --- | --- | --- | --- |
| 4E9-V10 | 3.08E−09 | 3.98E−11 | 1.73E+05 | 9.99E+02 | 5.34E−04 | 6.18E−06 | 0.236 | 0.9946 |
| 4E9-V13 | 3.41E−09 | 4.03E−11 | 1.66E+05 | 9.02E+02 | 5.65E−04 | 5.92E−06 | 0.1934 | 0.9956 |
| 4E9-V12 | 9.30E−09 | 1.55E−11 | 2.88E+04 | 1.20E+03 | 2.68E−04 | 4.33E−06 | 0.1415 | 0.9957 |
| 4E9-V6 | 3.05E−09 | 3.71E−11 | 1.66E+05 | 8.51E+02 | 5.06E−04 | 5.58E−06 | 0.2055 | 0.9963 |

KD: Affinity constant, in moles (M).
Ka: Association rate constant, in the reciprocal of molar time (1/Ms).
Kd: Dissociation rate constant, in the reciprocal of time.
$R^2$: Degree of fitting, that is, the degree of fitting between a measured curve and a fitted curve. The closer $R^2$ is to 1, the closer a fitted value is to the measured value, and in this system, $R^2$ should be at least greater than 0.95.
$X^2$: Statistical parameter performance of the values measured by the system, which should be less than 3, and the smaller it is, the more credible the measured value.

Other error values are the error values of their corresponding parameters, which should be an order of magnitude (10-fold) smaller than the corresponding parameters or less.

The results show that 4E9-V6 and 4E9-V10 have the lowest KD values, and the highest antigen affinity.

Based on the above results as well as the results of antibody function assay in cells and the results of physicochemical analysis, 4E9-V10 is the humanized single domain antibody with the best comprehensive effect among all the humanized sequences, which was unexpected by the inventors, and 4E9-V10 was used for assays in subsequent examples.

Example 5

Construction of Eukaryotic Expression Vector of Fc Fusion Antibody of Anti-IL-4Rα/IL-5 Protein Bispecific Single Domain Antibody (1) The gene sequence (positions 1-345 of SEQ ID NO. 23) of the codon-optimized humanized anti-IL-4Rα single domain antibody (4E9V10) or the gene sequence (positions 1069-1434 of SEQ ID NO. 23) of the humanized anti-IL-5 single domain antibody (named 2B3V2) were synthesized and inserted into a vector RJK-V4-3 (obtained referring to the method disclosed in the Chinese invention patent application no. CN202010576200.7 titled with "Anti-IL-4Rα single domain antibody as well as application and drug") respectively by means of sequence synthesis.

(2) The constructed recombinant eukaryotic expression vector was transformed into DH5a *Escherichia coli*, and cultured for plasmid maxiprep extraction and removal of endotoxin.

(3) The extracted plasmids were sequenced and identified.

(4) The identified anti-IL-4Rα antibody sequence was subcloned into the eukaryotic expression vector containing the anti-IL-S antibody sequence: specifically, the anti-IL-4Rα antibody sequence was cut from the eukaryotic expression vector where it was located by using restriction endonucleases Xba I and BamH I, and ligated with the eukaryotic expression vector containing the anti-IL-S antibody sequence with the same restriction endonuclease sticky end. The ligated vector was subjected to transformation, sequencing and identification; the clones confirmed by sequencing were subjected to plasmid maxiprep extraction for removal of endotoxin; the extracted plasmids were then sequenced and identified; and confirmed recombinant vectors were prepared for subsequent transfection and expression in eukaryotic cell. The eukaryotic expression vector of the anti-IL-4Rα/IL-5 protein bispecific single domain antibody was obtained. The anti-IL-4Rα/IL-5 protein bispecific single domain antibody (having an amino acid sequence shown in SEQ ID NO. 24, and a gene sequence shown in SEQ ID NO. 23) was named 4E9V10-2B3V2, and includes three moieties: 4E9V10-Fc fragment-2B3V2, where 4E9V10 is at the amino terminus (positions 1-115 in SEQ ID NO. 24), the Fc fragment is at positions 116-356 in SEQ ID NO. 24, and 2B3V2 is at the carboxy terminus (positions 357-478 in SEQ ID NO. 24).

Example 6

The anti-IL-4Rα/IL-5 protein bispecific single domain antibody was expressed in a suspension ExpiCHO-S cell by an assay method referring to the Chinese invention patent application no. CN202010576200.7 titled with "Anti-IL-4Rα single domain antibody as well as application and drug".

Example 7

The anti-IL-4Rα/IL-5 protein bispecific single domain antibody was expressed in a suspension 293F cell by an assay method referring to the Chinese invention patent application no. CN202010576200.7 titled with "Anti-IL-4Rα single domain antibody as well as application and drug".

Example 8

The anti-IL-4Rα/IL-5 protein bispecific single domain antibody was purified by an assay method referring to the Chinese invention patent application no. CN202010576200.7 titled with "Anti-IL-4Rα single domain antibody as well as application and drug".

Example 9

Blocking Assay of Receptor-Ligand Binding Using Bispecific Single Domain Antibody
(1) A receptor protein (IL-4Rα or IL-5R) was diluted with a protein diluent to 1 µg/mL, and coated overnight at 4° C.
(2) The plate was washed and blocked with 5% skim milk at 37° C.
(3) A biotin-conjugated ligand protein (IL-4 or IL-5) was diluted to 2 times the EC80 concentration, and the antibody was diluted to 2 times the initial concentration, and 5-fold gradient dilution was carried out. The ligand protein, and the diluted antibody (dupilumab, 4E9V10-2B3V2, 4E9-V0 or 2B3 (SEQ ID NO. 25)) and hIgG respectively, were transferred at 1:1 into a new dispensing plate and mixed well.
(4) The plate was washed, and the diluted ligand protein/antibody mixture was transferred into an ELISA plate in duplicate and incubated at 37° C.
(5) The plate was washed, and diluted Streptavidin[HRP] was added and incubated at 37° C.

Figures 5, 6:
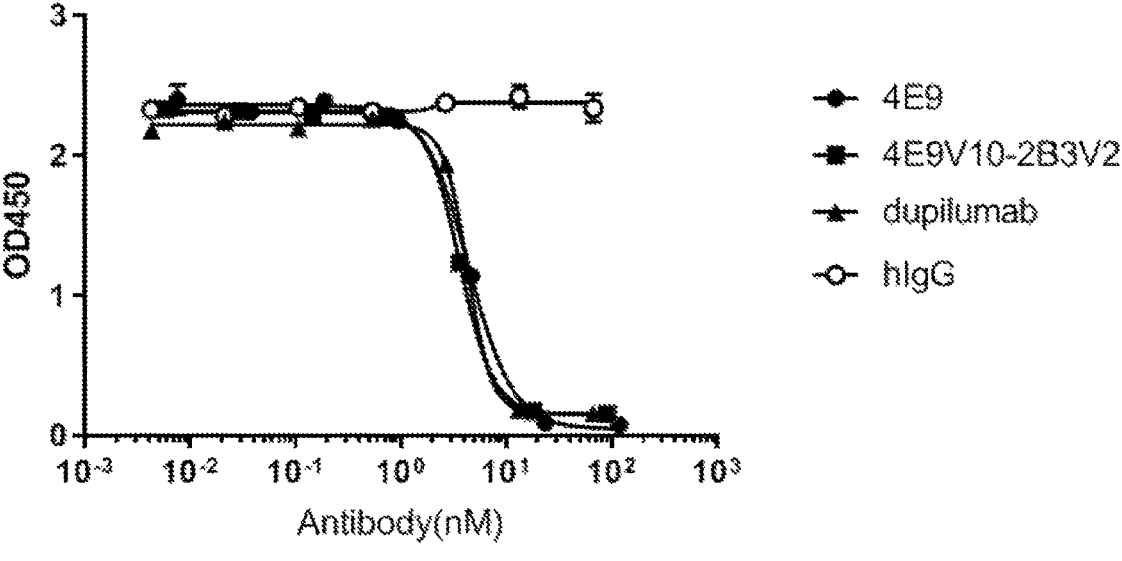
FIG. 5 shows assay results (ELISA) of an IL-4Rα/IL-5 bispecific antibody 4E9V10-2B3V2 blocking binding of IL-4Rα to IL-4.
FIG. 6 shows assay results (ELISA) of an IL-4Rα/IL-5 bispecific antibody 4E9V10-2B3V2 blocking binding of IL-5R to IL-5.

(6) The plate was washed, single-component TMB was added for color development at room temperature in the dark.
(7) A stopping solution was added, and the values of samples in different wells were immediately read at the wavelength of 450 nM with a microplate reader and recorded as OD450. EC50 was calculated by plotting. 4E9-V0, non-humanized anti-IL-S single domain antibody 2B3, dupilumab, reslizumab, and hIgG were used as controls, and the results are shown in Tables 6 and 7 and FIGS. 5 and 6, respectively.

TABLE 6

| Assay results of EC50 of bispecific antibodies blocking binding of IL-4 to IL-4Rα | | | |
|---|---|---|---|
| | 4E9-V0 | 4E9V10-2B3V2 | dupilumab | hIgG |
| EC50(nM) | 4.447 | 3.653 | 4.321 | 2.038 |

TABLE 7

| Assay results of EC50 of bispecific antibodies blocking binding of IL-5 to IL-5R | | | |
|---|---|---|---|
| | 2B3 | 4E9V10-2B3V2 | reslizumab | hIgG |
| EC50(nM) | 6.911 | 3.612 | 6.208 | 27387599489 |

The results show that the humanized bispecific antibody was non-attenuated and slightly advantageous in blocking IL-4/IL-4Rα or IL-5/IL-5R receptor-ligand binding than the non-humanized antibody. Compared with the corresponding commercial drugs, the humanized bispecific antibody has almost the same and slightly advantageous blocking ability.

Example 10

Figure 7:
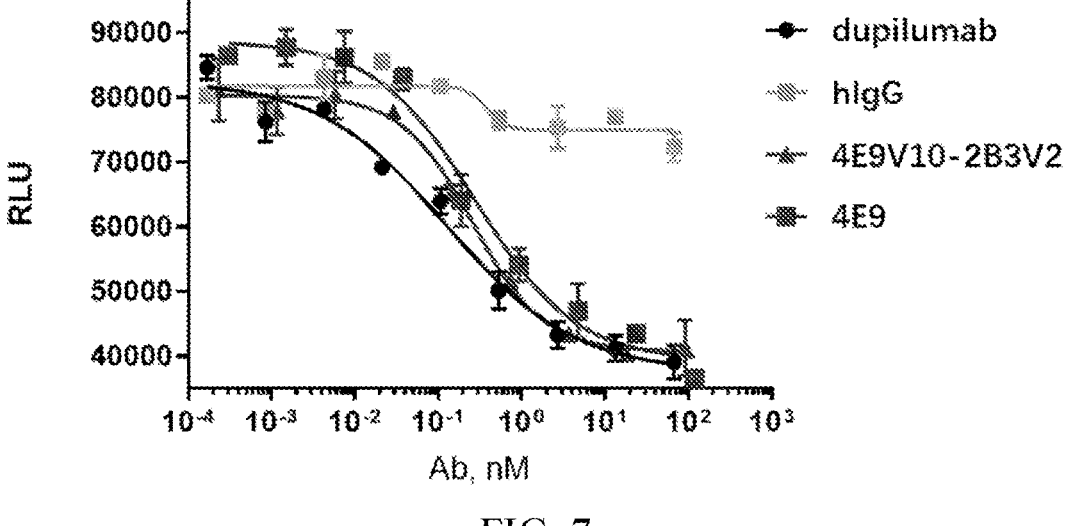
FIG. 7 shows assay results of an IL-4Rα/IL-5 bispecific antibody 4E9V10-2B3V2 neutralizing IL-4-induced TF-1 proliferation.
Figure 8:
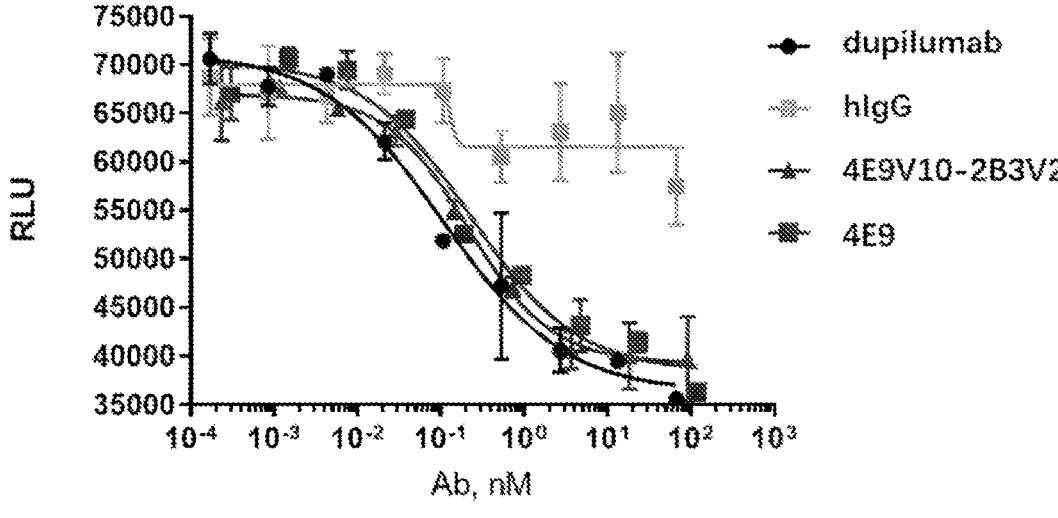
FIG. 8 shows assay results of an IL-4Rα/IL-5 bispecific antibody 4E9V10-2B3V2 neutralizing IL-13-induced TF-1 proliferation.

Neutralization Assay for IL-4-Induced or IL-13-Induced TF1 Cell Proliferation by Bispecific Single Domain Antibodies
Referring to Example 2 for the assay method.
The assay results are shown in Tables 8 and 9 and FIGS. 7 and 8.

TABLE 8

| Assay results of bispecific single domain antibodies neutralizing IL-4-induced TF-1 cell proliferation | | | |
|---|---|---|---|
| | 4E9-V0 | 4E9V10-2B3V2 | dupilumab | hIgG |
| EC50(nM) | 0.2812 | 0.2618 | 0.1297 | 0.3750 |

TABLE 9

| Assay results of bispecific single domain antibodies neutralizing IL-13-induced TF-1 cell proliferation | | | |
|---|---|---|---|
| | 4E9-V0 | 4E9V10-2B3V2 | dupilumab | hIgG |
| EC50(nM) | 0.2291 | 0.2154 | 0.1783 | 0.1312 |

The results show that the humanized bispecific antibody was non-attenuated and slightly advantageous in neutralizing IL-4-induced TF-1 cell proliferation than the non-humanized antibody. Compared with the corresponding commercial drugs, the humanized bispecific antibody has almost the same blocking ability.

Example 11

Assay for Human Recombinant IL-5 Protein-Induced TF1 Cell Proliferation and Tool Antibody (Tab) Neutralizing Proliferation A. Assay for Human Recombinant IL-5 Protein-Induced TF1 Cell Proliferation:

(1) TF-1 cells passaged 3-4 times after recovery were plated in a 96-well plate at 10000 cells/well.

(2) The human IL-5 protein was formulated into a solution with a maximum concentration of 500 ng/mL, and subjected to 5-fold gradient dilution.

(3) The IL-5 protein solution subjected to gradient dilution was added into cell culture wells in an equal volume to the cell culture solution.

(4) After incubation for 72 h, the cell viability was detected with a luminescence cell viability assay kit.

(5) The EC80 concentration for IL-S-induced TF-1 cell proliferation was calculated according to the assay results, and the calculated result was 2.96 ng/mL.

B. Assay for Tab Neutralizing Human IL-S-Induced TF1 Cell Proliferation (1) TF-1 cells passaged 3-4 times after recovery were plated into a 96-well plate at 10000 cells/well.

(2) The Tab was formulated into a solution of 10 µg/mL, and subjected to 5-fold gradient dilution.

(3) The Tab subjected to gradient dilution was mixed with the IL-5 at the EC80 concentration obtained in the proliferation assay at 1:1 to prepare a mixed solution.

(4) The mixed solution was added into cell culture wells in an equal volume to the cell culture solution.

(5) After incubation for 72 h, the cell viability was detected with a luminescence cell viability assay kit.

(5) After incubation for 72 h, the cell viability was detected with a luminescence cell viability assay kit.

Figure 9:
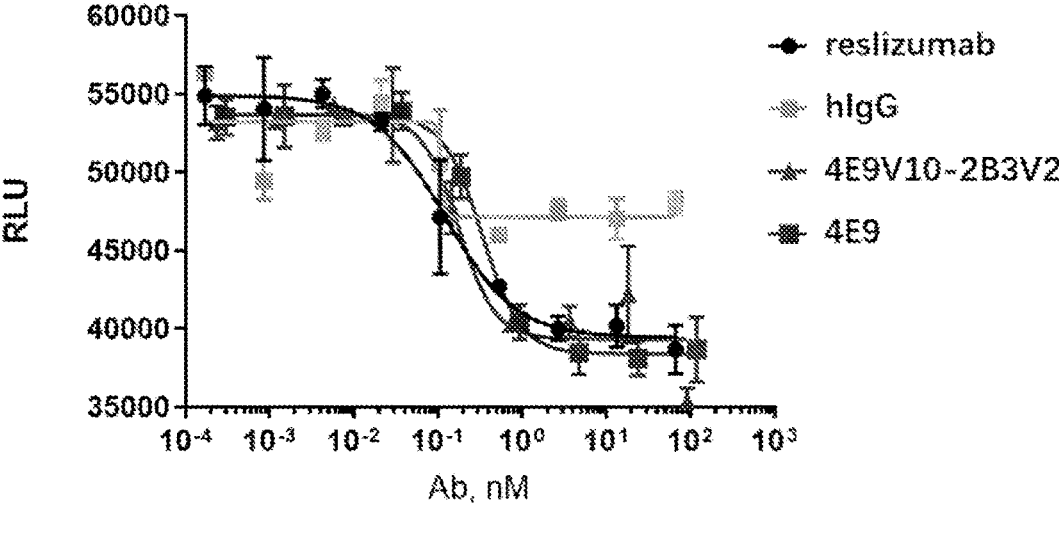
FIG. 9 shows assay results of an IL-4Rα/IL-5 bispecific antibody 4E9V10-2B3V2 neutralizing IL-5-induced TF-1 proliferation.

(6) The EC50 concentrations of different single domain antibodies neutralizing the IL-5-induced TF-1 cell proliferation were calculated according to the assay results, and the assay results are shown in Table 10 and FIG. 9.

TABLE 10

| Assay results of bispecific antibodies neutralizing IL-5-induced TF-1 cell proliferation | | | | |
| --- | --- | --- | --- | --- |
| | reslizumab | hIgG | 4E9V10-2B3V2 | 2B3 |
| EC50(nM) | 0.1221 | 0.1080 | 0.1753 | 0.3362 |

The results show that the humanized bispecific antibody was non-attenuated and slightly advantageous in neutralizing IL-5-induced TF-1 cell proliferation than the non-humanized antibody. Compared with the corresponding commercial drugs, the humanized bispecific antibody has almost the same blocking ability.

Example 12

Affinity kinetic assay for the humanized bispecific antibody was carried out by the assay method shown in example 4, and the assay results are shown in Table 11.

TABLE 11

| | Binding antigen | KD(M) | Ka(1/Ms) | Ka Error | Kd(1/s) | Kd Error | $R^2$ |
| --- | --- | --- | --- | --- | --- | --- | --- |
| 4E9V10-2B3V2 | IL-4Rα | 2.33E−10 | 1.98E+05 | 1.24E+03 | 4.60E−05 | 6.73E−06 | 0.994 |
| 4E9V10-2B3V2 | IL-5 | 6.63E−10 | 2.13E+05 | 1.29E+03 | 1.41E−04 | 5.84E−06 | 0.9905 |

(6) The EC50 concentration of the Tab neutralizing the IL-S-induced TF-1 cell proliferation was calculated according to the assay results.

Example 12

Assay for Humanized Bispecific Single Domain Antibodies Neutralizing IL-S-Induced TF1 Cell Proliferation.

(1) TF-1 cells passaged 3-4 times after recovery were plated into a 96-well plate at 10000 cells/well.

(2) The Tab and the aforementioned humanized bispecific single domain antibody were formulated into a solution of 10 µg/mL, and subjected to 5-fold gradient dilution.

(3) The Tab and the humanized antibody subjected to gradient dilution were mixed respectively with the IL-5 protein of the EC80 concentration obtained in example 13-A at 1:1 to prepare a mixed solution.

(4) The mixed solution was added into cell culture wells in an equal volume to the cell culture solution.

The results show that the affinity of the bispecific antibody targeting IL4Rα and IL-5 was determined with two antigens respectively, and the corresponding affinities were both below 1 nM.

The foregoing displays and describes basic principles, main features, and advantages of the present disclosure. A person skilled in the art may understand that the present disclosure is not limited to the foregoing embodiments. Descriptions in the embodiments and this specification only illustrate the principles of the present disclosure. Various modifications and improvements are made in the present disclosure without departing from the spirit and the scope of the present disclosure, and these modifications and improvements shall fall within the protection scope of the present disclosure. The protection scope of the present disclosure is subject to the appended claims and equivalents thereof.

What is claimed is:

1. A humanized anti-IL-4Rα single domain antibody, comprising complementarity determining regions comprising CDR1, CDR2 and CDR3 and framework regions comprising FR1, FR2, FR3 and FR4;

wherein CDR1 has an amino acid sequence as set forth in SEQ ID NO. 3, CDR2 has an amino acid sequence as set forth in SEQ ID NO. 12, and CDR3 has an amino acid sequence as set forth in SEQ ID NO. 18; and FR1 has an amino acid sequence as set forth in SEQ ID NO. 2, FR2 has an amino acid sequence selected from any one of SEQ ID NO. 4-11, FR3 has an amino acid sequence selected from any one of SEQ ID NO. 13-17, and FR4 has an amino acid sequence as set forth in SEQ ID NO. 20 or 21.

2. The humanized anti-IL-4Rα single domain antibody according to claim 1, wherein the amino acid sequence of FR2 is as set forth in SEQ ID NO. 11, the amino acid sequence of FR3 is as set forth in SEQ ID NO. 15, and the amino acid sequence of FR4 is as set forth in SEQ ID NO. 21.

3. A fusion protein comprising the anti-IL-4Rα single domain antibody according to claim 1.

4. A bispecific antibody comprising the anti-IL-4Rα single domain antibody according to claim 1.

5. A method for treating a disease in a subject, comprising administering the anti-IL-4Rα single domain antibody according to claim 1 to the subject, wherein the disease is selected from asthma, allergic dermatitis, eczema, arthritis, herpes, chronic primary urticaria, scleroderma, hypertrophic cicatrix, chronic obstructive pulmonary disease, atopic dermatitis, idiopathic pulmonary fibrosis, Kawasaki disease, sickle cell disease, Graves' disease, Sjogren's syndrome, autoimmune lymphoproliferative syndrome, autoimmune hemolytic anemia, Barrett's esophagus, autoimmune uveitis, tuberculosis, and nephropathy.

6. A drug for treating a disease, comprising the anti-IL-4Rα single domain antibody according to claim 1, and a pharmaceutically acceptable excipient.

7. An isolated nucleic acid molecule encoding the anti-IL-4Rα single domain antibody according to claim 1.

8. A vector or recombinant cell containing the nucleic acid molecule according to claim 7.

9. A method for preparing the anti-IL-4Rα single domain antibody according to claim 1, comprising: culturing a recombinant cell, and isolating and purifying the anti-IL-4Rα single domain antibody from the culture product, the recombinant cell containing a recombinant expression vector comprising a nucleic acid molecule encoding the anti-IL-4Rα single domain antibody.

* * * * *

SEQUENCE LISTING

<160> NUMBER OF SEQ ID NOS: 30

<210> SEQ ID NO 1
<211> LENGTH: 24
<212> TYPE: PRT
<213> ORGANISM: artificial sequence
<220> FEATURE:
<223> OTHER INFORMATION: framework region FR1 of humanized single domain
      antibody 4E9-V0

<400> SEQUENCE: 1

Gln Val Gln Leu Val Glu Ser Gly Gly Gly Ser Val Gln Ala Gly Gly
1               5                   10                  15

Ser Leu Arg Leu Ser Cys Ala Ala
            20

<210> SEQ ID NO 2
<211> LENGTH: 24
<212> TYPE: PRT
<213> ORGANISM: artificial sequence
<220> FEATURE:
<223> OTHER INFORMATION: framework region FR1 of the humanized
      anti-IL-4R alpha single domain antibody

<400> SEQUENCE: 2

Gln Val Gln Leu Val Glu Ser Gly Gly Gly Leu Val Gln Pro Gly Gly
1               5                   10                  15

Ser Leu Arg Leu Ser Cys Ala Ala
            20

<210> SEQ ID NO 3
<211> LENGTH: 6
<212> TYPE: PRT
<213> ORGANISM: artificial sequence
<220> FEATURE:
<223> OTHER INFORMATION: complementarity determining region CDR1 of the
      humanized anti-IL-4R alpha single domain antibody

<400> SEQUENCE: 3

Ser Gly Asp Phe Tyr Cys
1               5

<210> SEQ ID NO 4
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 4

Met Ala Trp Phe Arg Gln Ala Pro Gly Lys Glu Arg Glu Gly Val Ala
1               5                   10                  15

Thr

<210> SEQ ID NO 5
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 5

Leu Gly Trp Phe Arg Gln Ala Pro Gly Gln Gly Leu Glu Ala Val Ala
1               5                   10                  15

-continued

Ala

<210> SEQ ID NO 6
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 6

Leu Gly Trp Phe Arg Gln Ala Pro Gly Gln Glu Arg Glu Ala Val Ala
1               5                   10                  15

Ala

<210> SEQ ID NO 7
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 7

Met Ala Trp Phe Arg Gln Ala Pro Gly Lys Glu Arg Glu Ala Val Ala
1               5                   10                  15

Thr

<210> SEQ ID NO 8
<211> LENGTH: 16
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 8

Met Ala Trp Phe Arg Gln Ala Pro Gly Lys Glu Arg Glu Ala Val Ala
1               5                   10                  15

<210> SEQ ID NO 9
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 9

Met Ala Trp Phe Arg Gln Ala Pro Gly Lys Glu Arg Glu Arg Val Ala
1               5                   10                  15

Lys

<210> SEQ ID NO 10
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 10

Met Ala Trp Phe Arg Gln Ala Pro Gly Lys Glu Arg Glu Arg Val Ala
1               5                   10                  15

-continued

Thr

<210> SEQ ID NO 11
<211> LENGTH: 17
<212> TYPE: PRT
<213> ORGANISM: artificial sequence
<220> FEATURE:
<223> OTHER INFORMATION: framework region FR2 of the humanized
      anti-IL-4R alpha single domain antibody

<400> SEQUENCE: 11

Met Ala Trp Phe Arg Gln Ala Pro Gly Lys Glu Arg Glu Ala Val Ala
1               5                   10                  15

Ala

<210> SEQ ID NO 12
<211> LENGTH: 8
<212> TYPE: PRT
<213> ORGANISM: artificial sequence
<220> FEATURE:
<223> OTHER INFORMATION: complementarity determining region CDR2 of the
      humanized anti-IL-4R alpha single domain antibody

<400> SEQUENCE: 12

Ile Arg Ser Gly Gly Arg Ser Thr
1               5

<210> SEQ ID NO 13
<211> LENGTH: 38
<212> TYPE: PRT
<213> ORGANISM: artificial sequence
<220> FEATURE:
<223> OTHER INFORMATION: framework region FR3 of the humanized
      anti-IL-4R alpha single domain antibody

<400> SEQUENCE: 13

Tyr Tyr Ala Asp Ser Val Lys Gly Arg Phe Thr Ile Ser Lys Asp Asn
1               5                   10                  15

Ala Lys Asp Thr Leu Tyr Leu Gln Met Asn Ser Leu Lys Pro Glu Asp
            20                  25                  30

Thr Ala Met Tyr Tyr Cys
        35

<210> SEQ ID NO 14
<211> LENGTH: 38
<212> TYPE: PRT
<213> ORGANISM: artificial sequence
<220> FEATURE:
<223> OTHER INFORMATION: framework region FR3 of the humanized
      anti-IL-4R alpha single domain antibody

<400> SEQUENCE: 14

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 15
<211> LENGTH: 38
<212> TYPE: PRT
<213> ORGANISM: artificial sequence
<220> FEATURE:
<223> OTHER INFORMATION: framework region FR3 of the humanized anti-IL-4R alpha single domain antibody

<400> SEQUENCE: 15

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Lys Ala Glu Asp
            20                  25                  30

Thr Ala Val Tyr Tyr Cys
        35

<210> SEQ ID NO 16
<211> LENGTH: 38
<212> TYPE: PRT
<213> ORGANISM: artificial sequence
<220> FEATURE:
<223> OTHER INFORMATION: framework region FR3 of the humanized
      anti-IL-4R alpha single domain antibody

<400> SEQUENCE: 16

Tyr Leu Ala Asp Ser Val Lys Gly Arg Phe Thr Ile Ser Arg Asp Asn
1               5                   10                  15

Ser Lys Asn Thr Leu Tyr Leu Gln Met Asn Ser Leu Lys Ala Glu Asp
            20                  25                  30

Thr Ala Val Tyr Tyr Cys
        35

<210> SEQ ID NO 17
<211> LENGTH: 38
<212> TYPE: PRT
<213> ORGANISM: artificial sequence
<220> FEATURE:
<223> OTHER INFORMATION: framework region FR3 of the humanized
      anti-IL-4R alpha single domain antibody

<400> SEQUENCE: 17

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Lys Ala Glu Asp
            20                  25                  30

Thr Ala Val Tyr Tyr Cys
        35

<210> SEQ ID NO 18
<211> LENGTH: 12
<212> TYPE: PRT
<213> ORGANISM: artificial sequence
<220> FEATURE:
<223> OTHER INFORMATION: complementarity determining region CDR3 of the
      humanized anti-IL-4R alpha single domain antibody

<400> SEQUENCE: 18

Ala Val Gly Val Asp Gly Asn Cys Arg Asn Tyr Trp
1               5                   10

<210> SEQ ID NO 19
<211> LENGTH: 12
<212> TYPE: PRT
<213> ORGANISM: artificial sequence
<220> FEATURE:
<223> OTHER INFORMATION: complementarity determining region CDR3 of the
      humanized anti-IL-4R alpha single domain antibody

<400> SEQUENCE: 19

Ala Val Gly Val Asp Ala Asn Cys Arg Asn Tyr Trp

-continued

```
1               5                10
```

```
<210> SEQ ID NO 20
<211> LENGTH: 10
<212> TYPE: PRT
<213> ORGANISM: artificial sequence
<220> FEATURE:
<223> OTHER INFORMATION: framework region FR4 of the humanized
      anti-IL-4R alpha single domain antibody

<400> SEQUENCE: 20

Gly Gln Gly Thr Gln Val Thr Val Ser Ser
1               5                10

<210> SEQ ID NO 21
<211> LENGTH: 10
<212> TYPE: PRT
<213> ORGANISM: artificial sequence
<220> FEATURE:
<223> OTHER INFORMATION: framework region FR4 of the humanized
      anti-IL-4R alpha single domain antibody

<400> SEQUENCE: 21

Gly Gln Gly Thr Leu Val Thr Val Ser Ser
1               5                10

<210> SEQ ID NO 22
<211> LENGTH: 115
<212> TYPE: PRT
<213> ORGANISM: artificial sequence
<220> FEATURE:
<223> OTHER INFORMATION: anti-IL-4R alpha single domain antibody 4E9
      (named 4E9-V0)

<400> SEQUENCE: 22

Gln Val Gln Leu Val Glu Ser Gly Gly Gly Ser Val Gln Ala Gly Gly
1               5                10               15

Ser Leu Arg Leu Ser Cys Ala Ala Ser Gly Asp Phe Tyr Cys Met Ala
            20              25              30

Trp Phe Arg Gln Ala Pro Gly Lys Glu Arg Glu Gly Val Ala Thr Ile
        35              40              45

Arg Ser Gly Gly Arg Ser Thr Tyr Tyr Ala Asp Ser Val Lys Gly Arg
    50              55              60

Phe Thr Ile Ser Lys Asp Asn Ala Lys Asp Thr Leu Tyr Leu Gln Met
65              70              75              80

Asn Ser Leu Lys Pro Glu Asp Thr Ala Met Tyr Tyr Cys Ala Val Gly
            85              90              95

Val Asp Gly Asn Cys Arg Asn Tyr Trp Gly Gln Gly Thr Gln Val Thr
            100             105             110

Val Ser Ser
        115

<210> SEQ ID NO 23
<211> LENGTH: 1434
<212> TYPE: DNA
<213> ORGANISM: artificial sequence
<220> FEATURE:
<223> OTHER INFORMATION: gene sequence of the humanized anti-IL-5 single
      domain antibody

<400> SEQUENCE: 23
caagtgcaac ttgtggaatc aggaggagga tcagtgcaag caggaggatc acttagactt      60
tcatgcgcag catcaggaga tttctattgt atggcatggt ttagacaagc acctggaaag     120
```

-continued

```
gagagggaag gagtggcaac aatcagatca ggaggaagat caacatacta cgcagattca      180
gtgaaaggaa gatttacaat ctcaaaggac aatgcaaagg acaccctta ccttcaaatg       240 aactcactta aacctgaaga tacagcaatg tactactgcg cagtgggagt ggatggaaac      300
tgcagaaact actggggcca ggggacacaa gtgacagtgt catcagagag caagtacggc      360
cctccttgcc ccagctgccc cgcccccgag tttctgggag ccccagcgt gtttctgttt       420 cctcccaagc ccaaagacac actgatgatc agcagaaccc ccgaggtgac atgcgtggtg      480
gtcgacgtga gccaagaaga tcccgaggtg cagttcaact ggtatgtgga cggcgtggag      540
gtgcacaacg ccaagaccaa gcctagggag gagcaattca cagcaccta cagagtggtg       600 agcgtgctga ccgtgctgca ccaagactgg ctgaacggca aggagtataa gtgtaaggtg      660
agcaacaagg gcctccccag cagcatcgag aagaccatct ccaaggccaa gggccagcct      720
agggagcctc aagtgtacac actgcccccc agccaagagg agatgaccaa aaaccaagtg      780
tctctgacat gcctcgtgaa gggcttctat cccagcgaca tcgccgtgga gtgggagagc      840
aatggccagc ccgagaataa ctacaagacc accccccccg tgctcgactc cgatggcagc      900
ttctttctgt actctaggct gaccgtggac aagtctaggt ggcaagaggg aaacgtgttc      960
agctgttccg tgatgcacga ggctctgcac aaccactaca cccagaagag cctctctctg     1020
tctctgggaa aggagagcaa gtacggcccct ccttgcccca gctgccccca agtgcagctg     1080
gtggagagtg ggggcggtag cgtacaagcg ggcggcagcc tgagactgag ctgcgccgcc     1140
agcggcaaca ccttcagctt cagcacctac tgcatgggct ggttcagaca gagccccggc     1200
aaggagagag agggcagcct ggccaccatc tacgacgcca gcaccgccta cgccggcagc     1260
gtgaagggca gattcaccat cagcagagac aacagcaaga acatcctgta cctgcagatg     1320
aacaacctga gaccgagga caccgccgtg tactactgcg ccgccgccag atactgcatg      1380
ttctggagcc accccagcta ctggggccag ggcacccagg tgaccgtgag cagc          1434
```

```
<210> SEQ ID NO 24
<211> LENGTH: 478
<212> TYPE: PRT
<213> ORGANISM: artificial sequence
<220> FEATURE:
<223> OTHER INFORMATION: amino acid sequence of the anti-IL-4R alpha or
      IL-5 protein bispecific single domain antibody

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
            20                  25                  30

Trp Phe Arg Gln Ala Pro Gly Lys Glu Arg Glu Ala Val Ala Ala Ile
        35                  40                  45

Arg Ser Gly Gly Arg Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
            100                 105                 110

Val Ser Ser Glu Ser Lys Tyr Gly Pro Pro Cys Pro Ser Cys Pro Ala
        115                 120                 125
```

-continued

```
Pro Glu Phe Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser Gln Glu Asp Pro Glu Val Gln Phe Asn Trp Tyr Val
                165                 170                 175

Asp Gly Val Glu Val His Asn Ala Lys Thr Lys Pro Arg Glu Glu Gln
                180                 185                 190

Phe Asn Ser Thr Tyr Arg Val Val Ser Val Leu Thr Val Leu His Gln
                195                 200                 205

Asp Trp Leu Asn Gly Lys Glu Tyr Lys Cys Lys Val Ser Asn Lys Gly
    210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Gln Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
    275                 280                 285

Lys Thr Thr Pro Pro Val Leu Asp Ser Asp Gly Ser Phe Phe Leu Tyr
    290                 295                 300

Ser Arg Leu Thr Val Asp Lys Ser Arg Trp Gln Glu Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Leu Gly Lys Glu Ser Lys Tyr Gly Pro Pro Cys
                340                 345                 350

Pro Ser Cys Pro Gln Val Gln Leu Val Glu Ser Gly Gly Gly Ser Val
                355                 360                 365

Gln Ala Gly Gly Ser Leu Arg Leu Ser Cys Ala Ala Ser Gly Asn Thr
    370                 375                 380

Phe Ser Phe Ser Thr Tyr Cys Met Gly Trp Phe Arg Gln Ser Pro Gly
385                 390                 395                 400

Lys Glu Arg Glu Gly Ser Leu Ala Thr Ile Tyr Asp Ala Ser Thr Ala
                405                 410                 415

Tyr Ala Gly Ser Val Lys Gly Arg Phe Thr Ile Ser Arg Asp Asn Ser
                420                 425                 430

Lys Asn Ile Leu Tyr Leu Gln Met Asn Asn Leu Arg Ala Glu Asp Thr
    435                 440                 445

Ala Val Tyr Tyr Cys Ala Ala Ala Arg Tyr Cys Met Phe Trp Ser His
    450                 455                 460

Pro Ser Tyr Trp Gly Gln Gly Thr Gln Val Thr Val Ser Ser
465                 470                 475
```

<210> SEQ ID NO 25
<211> LENGTH: 122
<212> TYPE: PRT
<213> ORGANISM: artificial sequence
<220> FEATURE:
<223> OTHER INFORMATION: amino acid sequence of the dupilumab

<400> SEQUENCE: 25

```
Gln Val Gln Leu Val Glu Ser Gly Gly Gly Ser Val Gln Ala Gly Gly
1               5                   10                  15
```

```
Ser Leu Arg Leu Ser Cys Ala Ala Ser Gly Asn Thr Phe Ser Phe Ser
            20                  25                  30

Thr Tyr Cys Met Gly Trp Phe Arg Gln Ser Pro Gly Lys Glu Arg Glu
        35                  40                  45

Gly Ser Leu Ala Thr Ile Tyr Asp Gly Ser Thr Ala Tyr Ala Gly Ser
    50                  55                  60

Val Lys Gly Arg Phe Thr Ile Ser Val Asp Asn Ala Lys Asn Ile Leu
65                  70                  75                  80

Tyr Leu Gln Met Asn Asn Leu Lys Pro Glu Asp Thr Ala Met Tyr Tyr
                85                  90                  95

Cys Ala Ala Ala Lys Tyr Cys Met Phe Trp Ser Asp Pro Ser Tyr Trp
            100                 105                 110

Gly Gln Gly Thr Gln Val Thr Val Ser Ser
        115                 120
```

```
<210> SEQ ID NO 26
<211> LENGTH: 115
<212> TYPE: PRT
<213> ORGANISM: artificial sequence
<220> FEATURE:
<223> OTHER INFORMATION: anti-IL-4R alpha single domain antibody 4E9V10

<400> SEQUENCE: 26
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
            20                  25                  30

Trp Phe Arg Gln Ala Pro Gly Lys Glu Arg Glu Ala Val Ala Ala Ile
        35                  40                  45

Arg Ser Gly Gly Arg Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
            100                 105                 110

Val Ser Ser
        115
```

```
<210> SEQ ID NO 27
<211> LENGTH: 115
<212> TYPE: PRT
<213> ORGANISM: artificial sequence
<220> FEATURE:
<223> OTHER INFORMATION: anti-IL-4R alpha single domain antibody 4E9V6

<400> SEQUENCE: 27
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
            20                  25                  30

Trp Phe Arg Gln Ala Pro Gly Lys Glu Arg Glu Ala Val Ala Thr Ile
        35                  40                  45

Arg Ser Gly Gly Arg Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
```

```
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
                100                 105                 110

Val Ser Ser
        115

<210> SEQ ID NO 28
<211> LENGTH: 115
<212> TYPE: PRT
<213> ORGANISM: artificial sequence
<220> FEATURE:
<223> OTHER INFORMATION: anti-IL-4R alpha single domain antibody 4E9V11

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
                20                  25                  30

Trp Phe Arg Gln Ala Pro Gly Lys Glu Arg Glu Ala Val Ala Lys Ile
            35                  40                  45

Arg Ser Gly Gly Arg Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
                100                 105                 110

Val Ser Ser
        115

<210> SEQ ID NO 29
<211> LENGTH: 115
<212> TYPE: PRT
<213> ORGANISM: artificial sequence
<220> FEATURE:
<223> OTHER INFORMATION: anti-IL-4R alpha single domain antibody 4E9V12

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
                20                  25                  30

Trp Phe Arg Gln Ala Pro Gly Lys Glu Arg Glu Ala Val Ala Thr Ile
            35                  40                  45

Arg Ser Gly Gly Arg Ser Thr Tyr Leu Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
                100                 105                 110

Val Ser Ser
        115
```

```
<210> SEQ ID NO 30
<211> LENGTH: 115
<212> TYPE: PRT
<213> ORGANISM: artificial sequence
<220> FEATURE:
<223> OTHER INFORMATION: Alignment Consensus

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Asp Phe Tyr Cys Met Ala
            20                  25                  30

Trp Phe Arg Gln Ala Pro Gly Lys Glu Arg Glu Ala Val Ala Thr Ile
        35                  40                  45

Arg Ser Gly Gly Arg Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Lys Ala Glu Asp Thr Ala Val Tyr Tyr Cys Ala Val Gly
                85                  90                  95

Val Asp Gly Asn Cys Arg Asn Tyr Trp Gly Gln Gly Thr Leu Val Thr
            100                 105                 110

Val Ser Ser
        115
```